(12) United States Patent
Fauske

(10) Patent No.: US 6,435,710 B1
(45) Date of Patent: Aug. 20, 2002

(54) FOAM DETECTOR APPARATUS AND METHOD

(75) Inventor: Hans K. Fauske, Hinsdale, IL (US)

(73) Assignee: Fauske & Associates, Inc., Burr Ridge, IL (US)

(*) Notice: Subject to any disclaimer, the term of this patent is extended or adjusted under 35 U.S.C. 154(b) by 53 days.

(21) Appl. No.: 09/584,222

(22) Filed: May 31, 2000

Related U.S. Application Data

(63) Continuation-in-part of application No. 09/175,594, filed on Oct. 20, 1998.
(60) Provisional application No. 60/098,003, filed on Aug. 26, 1998.

(51) Int. Cl.$^7$ .............................................. G01N 25/00
(52) U.S. Cl. .......................................... 374/45; 374/54
(58) Field of Search .................... 374/45, 54; 73/866.5, 73/861.41, 60.11, 61.46

(56) References Cited

U.S. PATENT DOCUMENTS

| | | | |
|---|---|---|---|
| 4,398,836 A | | 8/1983 | Sitek |
| 4,424,559 A | * | 1/1984 | Lorincz et al. ............. 364/131 |
| 4,434,342 A | | 2/1984 | Schubring |
| 4,456,389 A | | 6/1984 | Regenass et al. |
| 4,670,404 A | | 6/1987 | Swift et al. |
| 4,686,307 A | * | 8/1987 | Farbood et al. ............. 560/205 |
| 4,846,584 A | | 7/1989 | Burch et al. |
| 4,883,759 A | * | 11/1989 | Hopkins ..................... 435/289 |
| 4,901,257 A | | 2/1990 | Chang et al. |
| 4,902,962 A | * | 2/1990 | Ishikawa ..................... 324/690 |
| 5,098,196 A | | 3/1992 | O'Neill |
| 5,229,075 A | | 7/1993 | Fauske |
| 5,363,471 A | | 11/1994 | Jones |
| 5,437,842 A | * | 8/1995 | Jensen et al. ................ 422/106 |
| 5,536,935 A | * | 7/1996 | Klotzsch et al. ........ 250/223 B |
| 5,672,289 A | | 9/1997 | O'Neill |
| 5,793,022 A | | 8/1998 | Klinck et al. |
| 5,824,886 A | | 10/1998 | Selby et al. |
| 5,868,859 A | * | 2/1999 | Hei et al. ...................... 134/18 |
| 6,078,729 A | * | 6/2000 | Kopel ......................... 392/402 |
| 6,347,884 B1 | * | 2/2002 | Faure et al. .................... 374/45 |

* cited by examiner

Primary Examiner—Diego Gutierrez
Assistant Examiner—Lydia M. De Jesús
(74) Attorney, Agent, or Firm—Greer, Burns & Crain, Ltd.

(57) ABSTRACT

A foam detector apparatus has a detector probe for detecting the presence of foam in a test sample, with the probe held above the test sample surface and indicating foaming when foam rises from the test sample surface and contacts the detector probe. The probe has a low thermal mass measuring surface for detecting contact with foam, with the measuring surface heated to a temperature above the tempering temperature of the test sample. When the liquid portion of the foam contacts the heated measuring surface, the temperature of the low thermal mass surface quickly drops to the tempering temperature of the sample, thereby indicating foam.

12 Claims, 6 Drawing Sheets

FOAM DETECTOR APPARATUS AND METHOD

CROSS REFERENCE

The present application is a continuation in part of co-pending U.S. application Ser. No. 09/175,594, filed Oct. 20, 1998; which claims the benefit of U.S. Provisional application No. 60/098,003 filed Aug. 26, 1998.

FIELD OF THE INVENTION

The present invention relates to laboratory testing devices. More particularly, the present invention relates to methods and apparatuses for detecting foaming from samples.

BACKGROUND OF THE INVENTION

It is known in the art to use laboratory reaction calorimeter devices to obtain design basis data for designing chemical process relief systems. Data obtained include adiabatic rates of temperature and pressure rise for very fast, runaway type reactions. These devices generally operate by heating a test sample contained in a test cell until a threshold of a reaction is detected. Once a reaction is under way, heaters are manipulated to balance heat losses from the test sample so that the sample may remain adiabatic as it reacts.

There are presently available several reaction calorimeters useful for the study of runaway reactions. An example includes the device of Fauske's U.S. Pat. No. 4,670,404. While this device offers general utility, it may tend to be a difficult, expensive, and cumbersome device to operate and maintain due to its relatively complicated configuration. A less expensive, simpler reaction calorimeter useful for obtaining relief system design basis data is described in detail in Fauske's later U.S. Pat. No. 5,229,075, the teachings of which are herein incorporated by reference.

Heretofore, prior art calorimeter devices, including those disclosed in Fauske's '404 and '075 patents, lack means and methods for characterizing the flow regime of a material. In particular, the flow regime of a material under given reaction conditions may be generally-characterized as foamy or non-foamy. As its name suggests, foamy system behavior is generally characterized as a tendency for the liquid level to swell or foam as a reaction occurs and vapor or gas is generated in the liquid bulk. A common example of foamy behavior would be soapy water as air is blown into it; a great deal of foam results. A non-foamy system, on the other hand, does not tend to produce significant liquid level swell or foam during a runaway excursion. Water without any soap additives, for instance, does not foam appreciably as air is blown into it.

It is not possible to predict whether a material may be characterized as foamy or non-foamy when under runaway reaction conditions based on physical property data alone. Further, no known prior art calorimeter systems or other bench scale systems are equipped to make flow regime characterizations, such as a determination of whether a reaction under given conditions may be characterized as foamy or non-foamy, other than by visual means. That is, the only method by which flow regime characterization such as foamy or non-foamy classification may be made is through visual observation. As this practice is not safe or practical for a reaction under runaway conditions, observation is not a practical means of obtaining relief system design basis data.

In terms of relief system design, the characterization of a system as foamy or non-foamy is of critical importance. A foamy system presents a much more challenging system to accommodate under runaway conditions than does a non-foamy system. A foamy system generally requires larger overall capacity, with larger diameter vent piping and larger capacity down stream relief system components. Without such accommodations foamy systems may result in pressure rises that exceed vessel design pressures and cause vessel failure. As there is presently no known available practical method or apparatus for determining whether a reactive system is foamy or non-foamy, current relief system design practice is to generally assume all systems are foamy and to thus design overly conservative relief systems in many cases.

Further, for a given foamy system, there are no calorimeter devices capable of determining at what point during a reaction foamy behavior begins. Such information would be of great value, as a relief system could potentially be designed to accommodate the reaction during its non-foamy stage, thereby resulting in a less extensive, less costly system.

There are of course applications in addition to relief system design applications that have a need for determining the foaminess or flow regime of a material.

In conclusion, an unresolved need in industry exists for a method and apparatus for characterizing a material's foaminess.

OBJECTS OF THE INVENTION

It is an object of the invention to provide a method and apparatus for characterizing a material's flow regime as foamy or non-foamy.

It is a further object of the invention to provide a calorimeter apparatus having foam detector meas.

It is a further object of the invention to provide a foam detector apparatus.

It is a still further object of the invention to provide a method for detecting foaming from a test sample.

SUMMARY OF THE INVENTION

The apparatus of the present invention generally comprises foam detection means for detecting the presence of foam in a test sample being heated. The foam detection means of the present invention preferably comprise a detector placed above the surface level of a test sample. As foam rises from the sample it will come into contact with the foam detector. The foam detector will then send a signal to a data recording medium that records the test sample temperature at which foam was detected.

The preferred foam-detector comprises a probe with a heater for heating the probe surface, and a temperature measurement means operatively connected to the probe surface for measuring its temperature. The probe is of relatively low thermal mass, so that the surface temperature will change rapidly when contacted with cooling media. When the probe surface is in a gaseous environment over the surface of the test sample, the surface is heated to an elevated temperature above the predicted tempering temperature of the components of the sample. When foam comes in contact with the heated surface, the liquid component of the foam quickly cools the surface of the probe through latent heat of vaporization effects as the liquid turns to vapor on contact with the heated surface. Consequently, the probe surface temperature rapidly falls to a temperature near to the tempering temperature of the liquid component of the foam due to evaporative cooling effect. The temperature of the probe surface at this time should approximately correspond to the measured temperature of the liquid.

An example embodiment of the present invention comprises foam detection means for detecting the presence of foam in a sample being tested in a calorimeter. The calorimeter generally comprises a test sample container for containing a test sample, heater means for heating the test sample in the sample container, and temperature measurement means for measuring the temperature of the test sample. The foam detection means of this example embodiment are generally as described above. As foam rises from the sample being tested in the calorimeter it will come into contact with the foam detector. The foam detector will then send a signal to a data recording medium that records the temperature, time, and pressure at which foam was detected.

The method of the invention generally comprises a method for determining the flow regime of a test sample as foamy or non-foamy. The method comprises the general steps of heating a test sample in a test sample container, placing a foam detector means above the test sample surface, and detecting the presence of foam with the foam detector means.

In a preferred embodiment of the method of the invention, the step of detecting the presence of foam comprises the steps of heating a measuring surface of the detector probe to a temperature above the tempering temperature of the test sample, measuring the temperature of a measuring surface on the detector probe, and indicating the presence of foam when foam contacts the measuring surface and thereby causes the measuring surface temperature to fall to a temperature near the sample tempering temperature. Preferably, the detector probe measuring surface is comprised of low thermal mass glass.

The above brief description sets forth rather broadly the more important features of the present disclosure so that the detailed description that follows may be better understood, and so that the present contributions to the art may be better appreciated. There are, of course, additional features of the disclosure that will be described hereinafter which will form the subject matter of the claims appended hereto. In this respect, before explaining the several embodiments of the disclosure in detail, it is to be understood that the disclosure in not limited in its application to the details of the construction and the arrangements set forth in the following description or illustrated in the drawings. The present invention is capable of other embodiments and of being practiced and carried out in various ways, as will be appreciated by those skilled in the art. Also, it is to be understood that the phraseology and terminology employed herein are for description and not limitation.

The objects of the invention have been well satisfied. These advantages and others will become more fully apparent from the following detailed description when read in conjunction with the accompanying drawings.

DETAILED DESCRIPTION

While the methods and apparatus of the present invention are capable of being used in different applications, a description of a preferred form of apparatus will be given. This preferred apparatus embodiment comprises a calorimeter having a foam detector means. The preferred method of the invention will likewise be illustrated to those knowledgeable in the art through this discussion. Absent the foam detector, the general configuration of the test apparatus of the calorimeter of the present invention is known in the art. In particular, the teachings of Fauske's U.S. Pat. No. 5,229,075 are herein incorporated by reference for purposes of describing the preferred test apparatus configuration, absent the foam detector, of the preferred embodiment of the present invention.

As will be apparent to those knowledgeable in the art, the apparatus of the present invention is not limited to practice with the calorimeter apparatus as taught in Fauske's '075 patent. Other embodiments of the apparatus of the invention may comprise a foam detector probe in use with other instruments in addition to calorimeters. Further, the present invention may comprise a stand alone foam detector apparatus. For example, an embodiment of the foam detector apparatus of the invention may comprise a test sample container for containing the test sample, heater means for heating the test sample in the container, temperature measurement means for measuring the test sample temperature, and a foam detector probe for detecting the presence of foam in the test sample.

The foam detector probe preferably comprises a detector probe with a low thermal mass measuring surface, heating means for heating the measuring surface to a temperature in excess of a test sample tempering temperature, temperature measurement means for measuring the temperature of the measuring surface. The preferred detector probe operates with the measuring surface heated to a temperature above the tempering temperature of the test sample, and foaming detected when the liquid component of foam comes into contact with the measuring surface thereby causing it to quickly cool to the tempering temperature as heat is lost through latent heat of vaporization effects.

Figure 1:
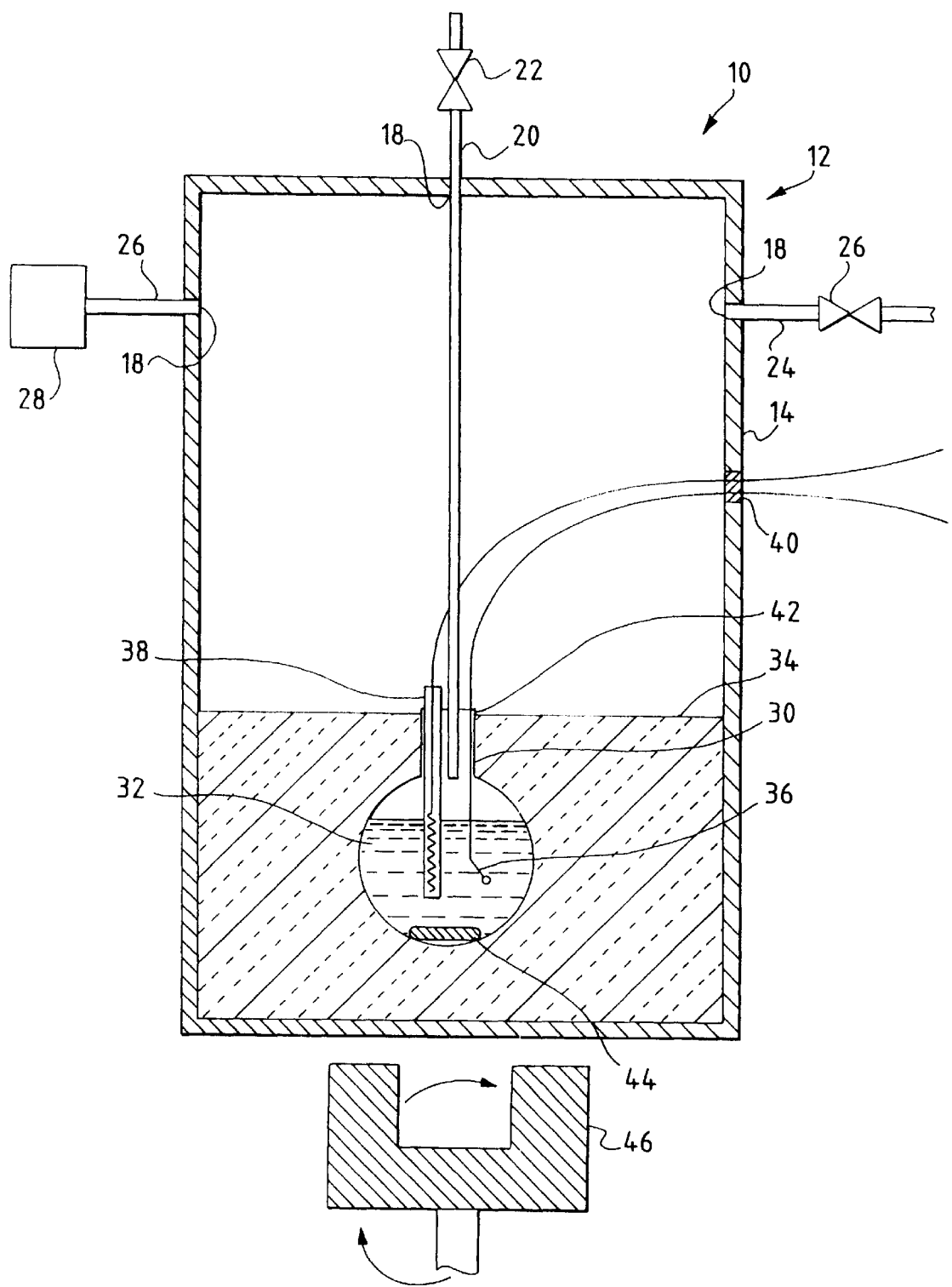
FIG. 1 is a cross section of the preferred test vessel configuration of the invention.

A preferred foam detector apparatus of the invention comprises a calorimeter device featuring a foam detector probe. Accordingly, referring now to the drawings, FIG. 1 shows a test apparatus 10 for carrying out the method of present invention as generally described by Fauske's '075 patent. As shown, the apparatus 10 includes an exterior containment vessel 12 with walls 14. Containment vessel 12 is sealable to insure pressure tightness of the interior. Suitable openings 18 are provided respectively in one or more of the walls 14 for passage of a fill pipe 20 with valve 22, atmosphere control pipe 24 with valve 26, and a pressure measurement pipe 26 with pressure measurement means 28. Preferred pressure measurement means 28 comprise a common commercial strain gage pressure transducer as is available from the Ashcroft Co. Atmosphere control pipe 24 with valve 26 may be connected to a isolatable vent source and/or an isolatable pad gas source, and may be useful to control the pressure in vessel 12 interior, as may be desirable to perform various relief system design experiments, as is explained at length in Fauske's '075 patent.

Test cell 30 contains the test sample material 32. Preferred test cell 30 is comprised of thin glass and is generally spherical in nature, with an open top neck for introduction of material. As taught by Fauske's '075 patent, it is preferred that the thermal mass of test cell 30 be low in comparison to the thermal mass of test material 32, where thermal mass is defined as mass multiplied by specific heat. The ratio of thermal mass of test cell 30 to test material 32 is preferably less than 1:6; is more preferably less than 1:8; and is most preferably less than 1:10. These ratios insure a minimal heat sink effect of test cell 30 on test material 32 as it reacts and generates heat. As explained in detail in Fauske's '075 patent, these ratios insure a "phi factor" that is comparable to that which occurs on an industrial chemical process scale, and thus allows for data from the apparatus of the invention to be applied directly to an industrial process scale.

To further help minimize heat losses, test cell 30 is surrounded by insulating material 34, which may preferably comprises glass fiber insulation or other materials with good thermal insulating properties. Temperature probe 36 is immersed directly in test material 32 to measure the temperature thereof. Temperature probe 36 preferably comprises a stainless steel type K thermocouple with a mini connector, but may also comprise a glass coated probe or metal alloy material as may be required for test material 32 compatibility. Shaft diameter for probe 36 is preferably 3/16" or less to insure rapid response to temperature change.

Test material 32 is heated using heater 38, which preferably comprises an electrical resistance coil contained in a glass sheath. Other heaters could be used, for example electrical resistors contained in a flat foil wrap which is attached to the exterior of test cell 30. Heater 38 is preferably powered by a DC power supply. Temperature probe 36 and heater 38 send and receive signals through vessel wall 14 at gland 40. Temperature probe 36 and heater 38 are attached to test cell 30 at its top rim 42. Material may be conveniently introduced to test cell 30 through fill line 20. Agitation of test sample material 30 is provided by magnetic stir bar 44 which spins in cooperation with spinning magnet 46 located external to vessel 10.

Figure 2:
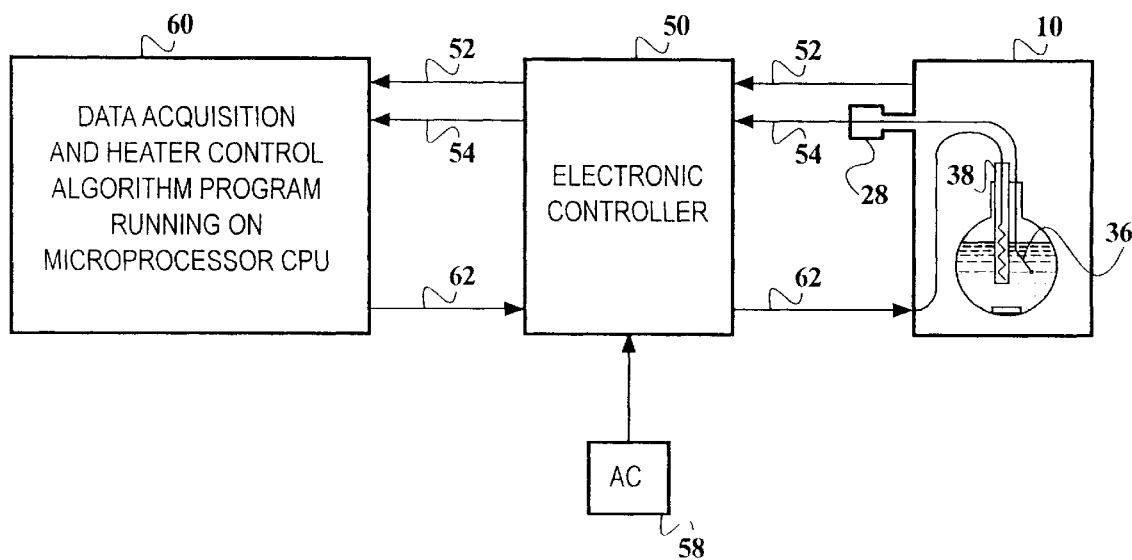
FIG. 2 is a block schematic diagram of a preferred overall apparatus of the invention.

FIG. 2 shows the general configuration of the calorimeter apparatus as taught by Fauske's '075 patent. Vessel 10 is connected to electronic controller 50. Electronic controller 50 provides a heater power supply, and temperature and pressure signal amplifiers and power supplies as may be required. Connection 52 relays temperature data from probe 36 to controller 50, connection 54 relays pressure data from pressure transducer 28, and connection 56 relays heater power from controller 50 to vessel 10 and its heater 38. Connections 52, 54, and 56 are preferably made using insulated cables and connectors as are known in the art and are widely commercially available. Electronic controller 50 is powered by a standard 110 V AC power source 58.

The preferred data acquisition and method of heater control comprise a computer program running on microprocessor based computer 60. Computer 60 is connected via connections 52, and 54, to receive temperature and pressure data respectively from controller 50. Connection 62 relays a heater control signal from the method of heater control running on computer 60 to controller 50. In addition to heater control, computer 60 may be programmed to record time and temperature data as described in the '075 reference, and to control various additional features of the test apparatus as may be required.

Figure 3:
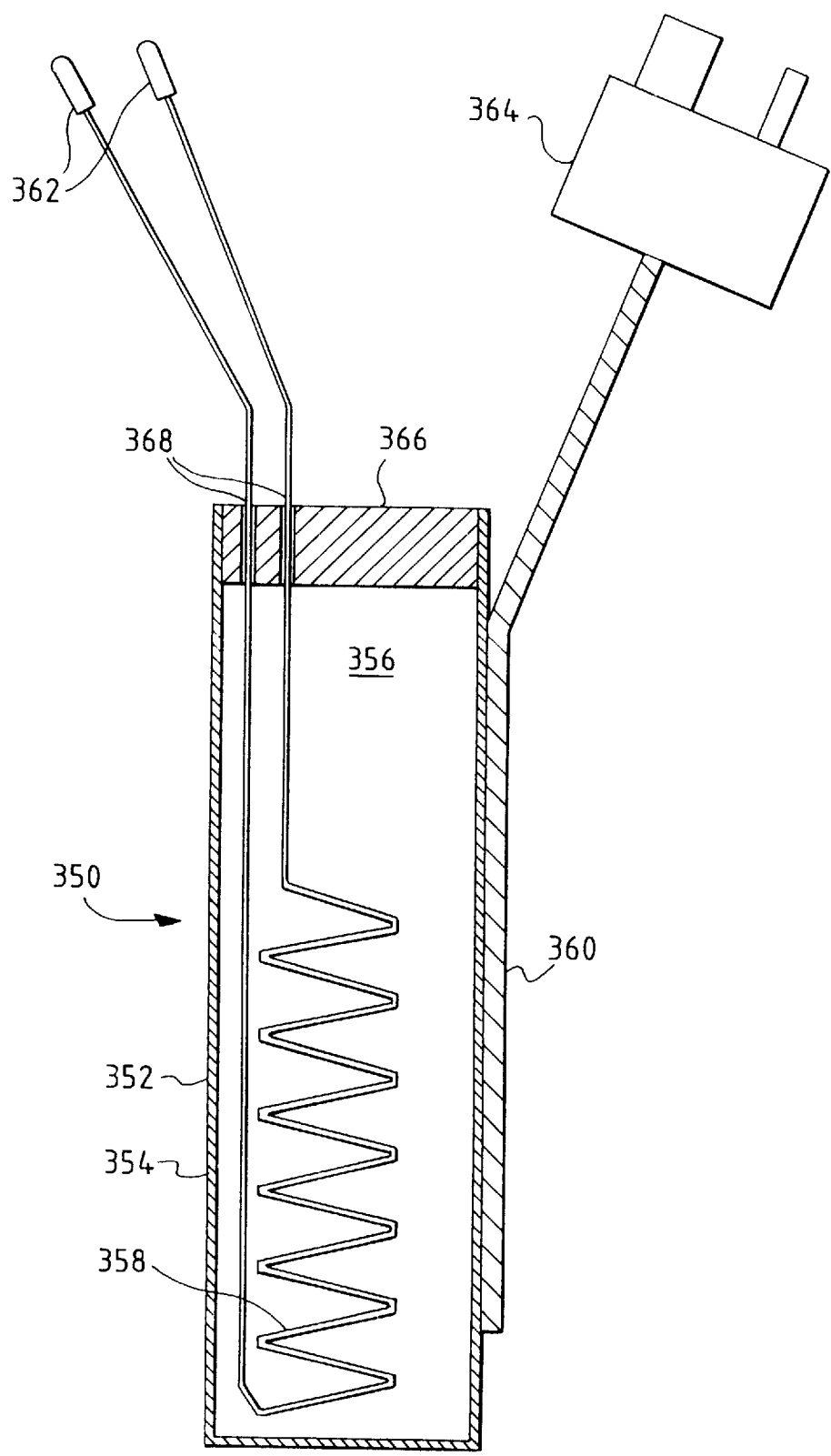
FIG. 3 is a cross sectional view of a preferred foam detector probe of the invention.

The calorimeter apparatus as described heretofore with reference to FIGS. 1 and 2 is generally known in the art, and is as described in Fauske's '075 patent. In addition to the calorimeter as is known, however, a preferred embodiment of the apparatus of the present invention further comprises a foam detector means for detecting the presence of foam in a sample being tested in the calorimeter. FIG. 3 shows a preferred foam detector means of the present invention. It comprises cylindrical probe 350 made of glass with thin walls 352 and probe surface 354. The interior 356 of probe 350 contains heater resistor coil 358 for heating walls 352 and thereby probe surface 354. Thermocouple 360 is attached to probe surface 354 to measure surface temperature. Preferred thermocouple 360 is a type K with a stainless steel shaft of no more than 3/16" diameter for rapid response to temperature changes. Heater coil 358 is connected to a DC power source via connectors 362; thermocouple 360 likewise connects to a device for reading and recording temperature via connector 364. Connectors 362 and 364 may be of any configuration, many of which are known in the art and commercially available, preferred connectors comprise miniature plug type connectors 362, and a miniature K type thermocouple connector 364. Interior 356 is sealed with plug 366, with pressure fit passages 368 allowing passage of heater coil 358 leads therethrough.

Figure 4:
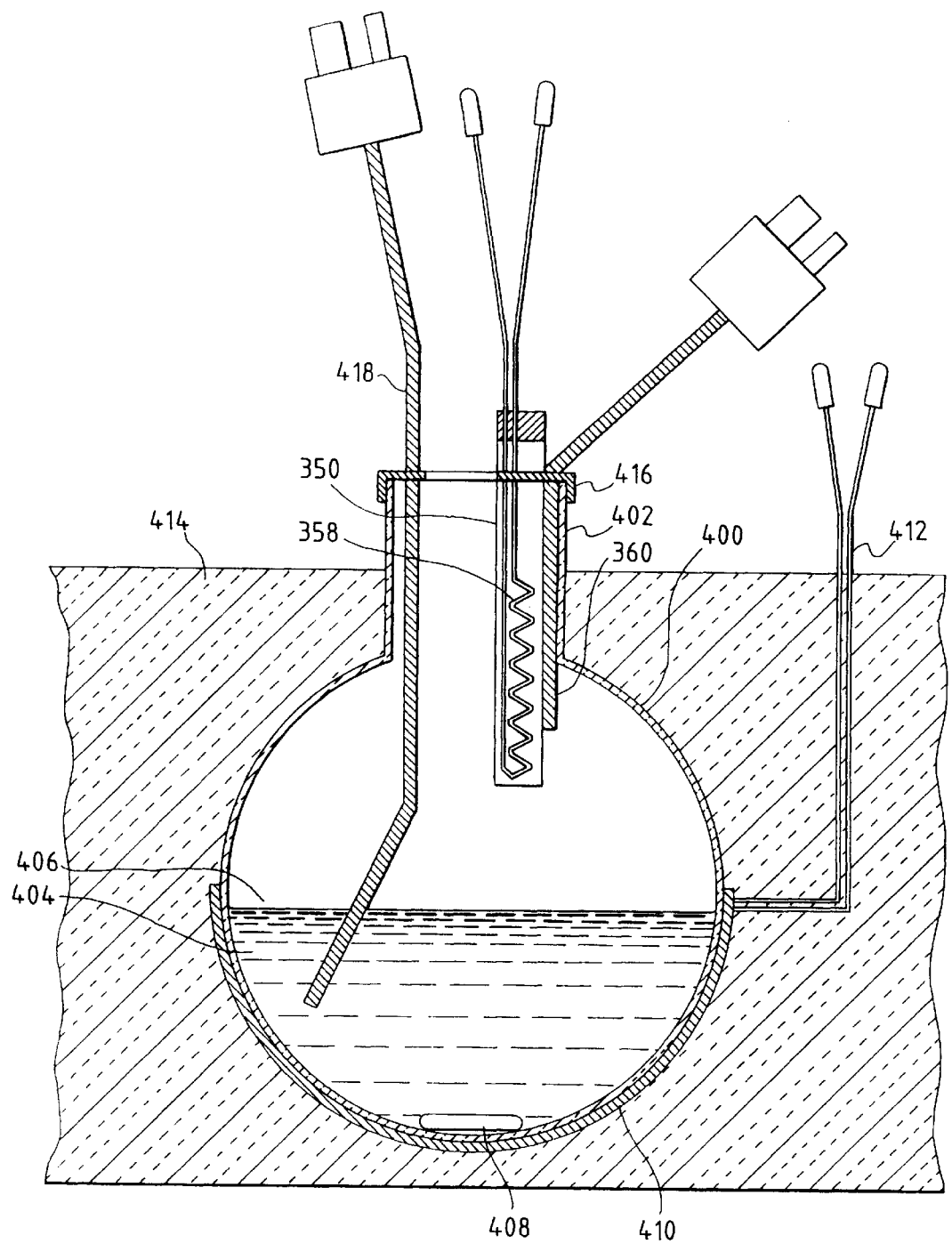
FIGS. 4 and 5 are cross sectional views of the preferred foam detector of the invention in use in the calorimeter of the invention.

FIG. 4 shows a cross sectional view of the preferred foam detector of the invention configured in the preferred test cell configuration as described herein, and as substantially described in Fauske's '750 patent. The present configuration includes spherical test cell 400 with open cylindrical neck 402. Test cell 400 contains test sample liquid 404 with surface 406. Test sample 404 is agitated with magnetic stirrer 408, which is driven by a spinning external magnet (not shown).

FIG. 4 shows an external heater 410 for heating the sample, which is an alternate to heater 38 to that of FIG. 1. External heater 410 comprises a flat foil wrap surrounding an electrical resistance element. External heater 410 is wrapped about the outside lower surface of test cell 400. External heater 410 has electrical leads 412, which extend through glass fiber insulation 414 which surrounds test cell 400.

Preferred foam detector 350 as illustrated in FIG. 3 is located in the open test cell neck 402 and above test sample surface 406 of FIG. 4. Foam detector 350 may be held in place using clip 416 mounted on test cell neck 402. During a test, test sample 404 is heated using external heater 410 to initiate an exothermic reaction or other event. Sample thermocouple 418 is immersed directly in test sample 404 to measure its temperature. Foam detector 350 is heated with coils 358 such that probe surface 352 temperature as measured by probe thermocouple 360 is in excess of a predetermined tempering temperature of components of test sample 404. For instance, if sample 404 is aqueous, then detector probe surface 352 would be heated to a temperature in excess of 100° C. Preferably, probe surface is heated to a temperature of at least 10° C. greater than the sample tempering temperature.

Thermocouple 360 sends an output signal to any suitable device for converting, displaying, and/or recording as is generally known in the art. Power for heater coil 358 is preferably DC, and may be supplied in any manner as is known in the art. An AC/DC converter may, for instance, be connected in sequence with a variable resistor and an AC power supply, with the resistor being manually adjusted until probe surface temperature as indicated by thermocouple 360 reaches its desired level. Alternatively, a controller circuit may be constructed that automatically powers heater coil 358 based on an input set temperature, with that set temperature being compared to thermocouple 360 reading which may be input to the controller. The preferred foam detector of the present invention will have heater power supply and thermocouple signal conditioning in the same electronic controller as is used to condition test sample thermocouple and power test sample heater, with automated control of the probe heater and data acquisition performed by a control algorithm running on the same microprocessor based computer as is used for the calorimeter of the invention.

Figure 5:
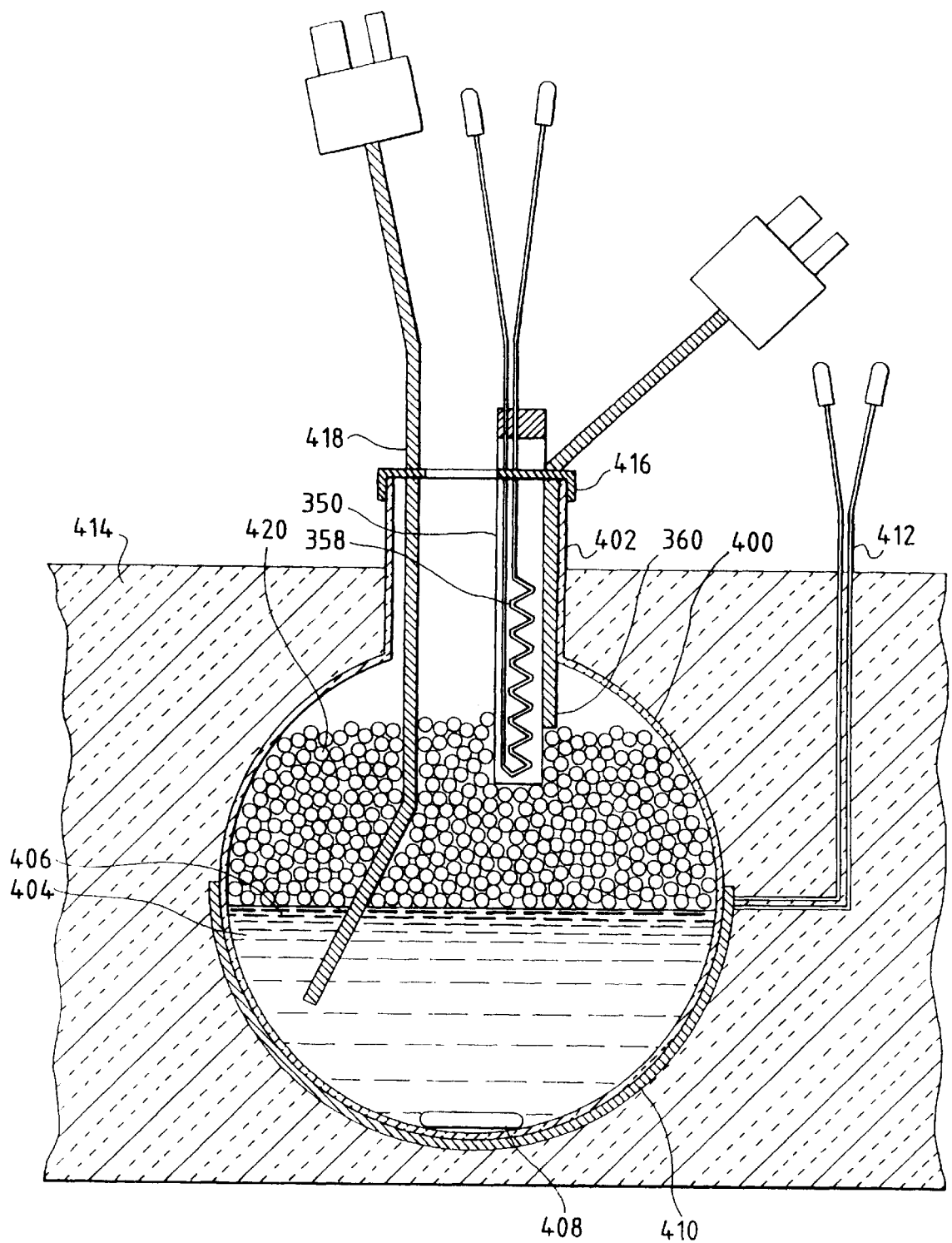

Fig. 5 illustrates the configuration of FIG. 4 as sample 404 is heated to a temperature at which foaming occurs. Foam 420 comes into contact with probe 350. As the liquid component of foam 420 comes into contact with the surface of probe 350 which is at a temperature in excess of the tempering temperature of that liquid component, the liquid component of the foam boils. When this contact occurs and boiling occurs, the liquid component of the foam draws energy from the probe surface corresponding to the latent heat of vaporization of the liquid. When the probe surface looses this energy, the surface temperature drops to the tempering temperature of the liquid. Thermocouple 360 detects this drop in temperature, thereby indicating foam presence. Temperature of the liquid test sample at this point as indicated by sample thermocouple 418 will indicate at what temperature the sample evolved foam.

Foam detector 350 surface should be of limited thermal capacity so that its temperature will quickly respond to contact with the liquid foam component cooling media. Likewise, the temperature above the sample tempering temperature to which detector 350 surface is heated to will have an effect on the temperature drop measured. As an example, using an aqueous sample, detector 350 surface will preferably be heated to a temperature of at least 110–130° C., and more preferably to at least 150° C., so that cooling will be readily apparent when contact with the aqueous water component of foam occurs.

Figure 6:
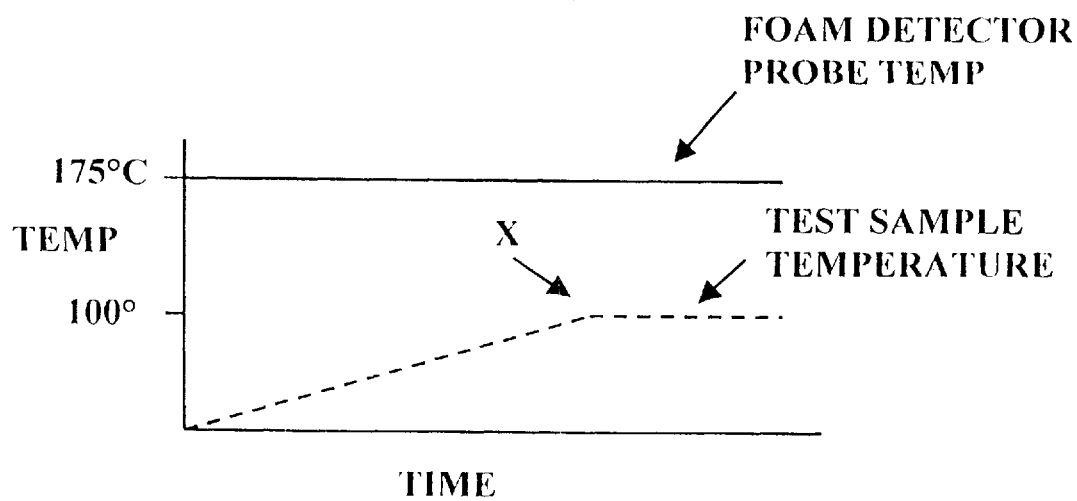
FIGS. 6 and 7 are data plots displaying data from the preferred foam detector of the invention.
Figure 7:
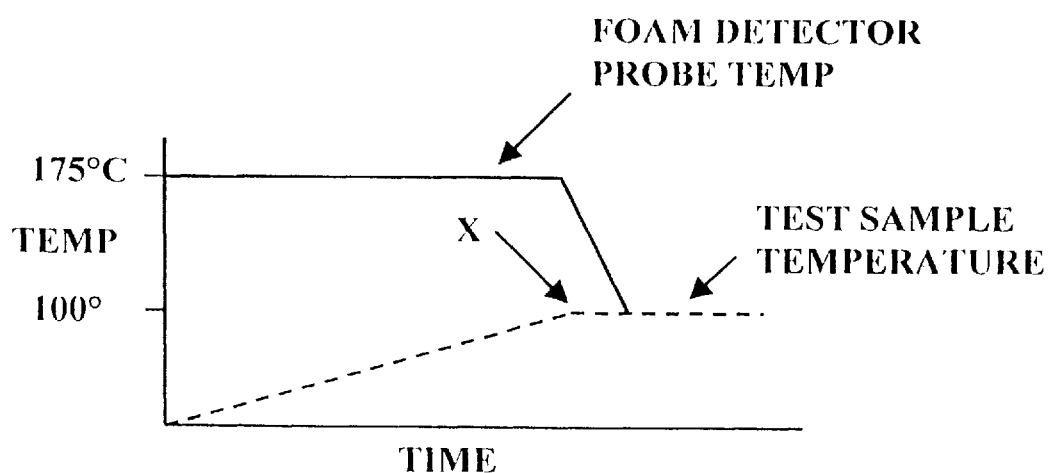

By way of illustrating the method of operation of the apparatus of the invention, FIGS. 6 and 7 show data plots resulting from the preferred foam detector of the invention, with FIG. 6 showing a non-foamy mixture of water being heated under atmospheric pressure, and FIG. 7 showing a foamy water with soap mixture. In FIG. 6, the foam detector probe is -heated to a temperature of 175° C., which is substantially in excess of water's tempering temperature of 100° C. The water sample is heated using the sample heater until it reaches 100< C., as indicated by point X in FIG. 6. The sample is preferably heated at a rate of less than 10° C./min, so that an accurate sample temperature will be known when foaming is detected. As indicated, at 100° C. the sample temperature becomes constant as water vaporizes. Foam detector temperature does not change at this point, indicating that no foam is present. In a soapy water solution, however, foaming would be expected as boiling occurred. Accordingly, in the plot of FIG. 7 for a soapy water solution, as boiling begins at 100° C. also indicated by point X, foam detector probe temperature quickly falls from its original temperature of 175° C. to 100° C. This occurs as the water component of the foam hits the detector probe and boils, sapping the probe of heat energy which is transferred into latent heat of vaporization energy by the water.

Thus the foam detector apparatus and the method of the invention may be used to determine the presence of foam, and the temperature at which foamy behavior begins to occur. This information may be used to great advantage for designers of process relief systems, as well as for additional purposes as will be appreciated by those knowledgeable in the art.

Other embodiments of the foam detector of the invention may comprise configurations other than those discussed above in reference to the preferred embodiment. As an example, other detector embodiments may be comprised of materials other than glass. Glass is preferred as it offers excellent anti-corrosion properties, and corrosion during a test is of course most disadvantageous. Also, glass is of relatively low thermal mass, is relatively inexpensive, and is relatively easy to work with. There are of course other materials, including alloys, polymers, and ceramics suitable for use in the apparatus of the invention.

It is also noted that the probe measuring surface need not comprise the entire surface of the probe. That is, a measuring surface may be comprised for detecting contact with foam that is not the entire surface of the probe. As an example, a small portion of the probe surface may comprise the measuring surface. The smaller measuring surface advantageously would require less energy for heating, thereby allowing for smaller heater mans to be used.

Further, it will be appreciated that the foam detector of the present invention is not limited to the example cylindrical shape described herein. An additional embodiment of the apparatus of the invention, as an example, may comprise a small wafer with temperature measurement means and heater means contained therein, with the wafer comprised of glass or other low thermal mass material. The cylindrical shape is preferred when using the spherical test cell illustrated herein, as it may be inserted in the spherical test cell neck. A spherical test cell is preferred for a few different considerations. First, it provides a rounded bottom which reduces friction with a magnetically driven stir bar for agitating the test sample. More particularly considering foam detection, the spherical shape is advantageous as it tends to have a "funneling" effect on the foam as it rises from the test sample surface. This funneling effect causes the foam to rise faster and to be more concentrated, which is advantageous for detection by the probe.

Further, the foam detector of the present invention need not comprise the preferred temperature measurement means comprising a thermocouple as described herein. As will be appreciated by those knowledgeable in the art, a wide variety of temperature measurement means are widely commercially available that would prove suitable for use with the detector probe of the present invention. It is preferred that any temperature measurement means used achieve rapid response time.

Other embodiments of the foam detector of the invention may comprise heated metal elements with a temperature measurement probe attached that operates in the same general manner as the preferred foam detector. Still other embodiments of the foam detector of the invention may comprise probes that detect contact with foam by means other than latent heat of vaporization cooling, such as by measuring a change in conditions other than temperature as foam contacts a surface or enters a measuring chamber. As an example, a detector probe may comprise a measuring chamber in which conditions are measured. Cooperating electrical elements, for instance, may operate across the chamber measuring the conductivity across the chamber. As foam enters the chamber, conductivity changes, and foaming is indicated. As another example, optical conditions across the chamber may be measured by cooperating optical elements. The elements may transmit a light beam across the chamber. As foam enters the chamber, the light beam is interfered with, and foam presence thereby detected.

The advantages of the disclosed invention are thus attained in an economical, practical, and facile manner. While preferred embodiments and example configurations have been shown and described, it is to be understood that various further modifications and additional configurations will be apparent to those skilled in the art. It is intended that the specific embodiments and configurations herein disclosed are illustrative of the preferred and best modes for practicing the invention, and should not be interpreted as limitations on the scope of the invention as defined by the appended claims.

What is claimed is:

1. A foam detector apparatus for detecting the foaminess of a sample, the apparatus comprising:
   a) a test sample container for containing the test sample;
   b) heater means for heating the test sample in said sample container, said test sample having a tempering temperature;
   c) temperature measurement means for measuring the test sample temperature; and
   d) foam detector means for detecting the presence of foaming in the test sample, said foam detector means comprising a detector probe placed above the sample surface, said detector probe having a measuring surface comprised of a low thermal mass material, a heater means for heating said measuring surface to a temperature above the test sample tempering temperature and a temperature measuring means for substantially continuously measuring the temperature of said measuring surface, wherein said detector probe indicates the presence of foam when said foam contacts said measuring surface, thereby cooling said measuring surface.

2. A foam detector apparatus as in claim 1, wherein said detector probe measuring surface is comprised of glass.

3. A foam detector apparatus as in claim 1, wherein said detector probe is substantially cylindrical and is comprised of glass, said substantially cylindrical probe having an outer surface, said measuring surface comprising at least a portion of said cylindrical outer surface.

4. A foam detector probe as in claim 3, wherein said measuring surface heater means comprises an electrical heater contained in said cylindrical probe, and wherein said measuring surface comprises a thermocouple means in operative contact with said measuring surface.

5. A foam detector apparatus for detecting the presence of foam from a test sample, the test sample having a tempering temperature, the apparatus comprising:
   a) a test sample container, sample heater means for heating the test sample, sample temperature measurement means for substantially continuously measuring the sample temperature;
   b) a foam detector probe, said detector probe having a measuring surface comprised of glass, having probe heater means for heating said measuring surface to a temperature above the sample tempering temperature, having probe temperature measuring means for measuring the temperature of said probe measuring surface, whereby said foam detector indicates the presence of foam when foam contacts said measuring surface and thereby cools said measuring surface.

6. A foam detector apparatus as in claim 5, wherein said apparatus further comprises:
   a) a sealable containment vessel for containing the test sample, said test sample holder, and said foam detector probe.

7. A foam detector apparatus as in claim 5, wherein said detector probe comprises a substantially cylindrical glass probe, said measuring surface comprising at least a portion of said cylindrical probe outer surface, said probe heater comprises an electrical heater held within said substantially cylindrical probe, and said probe temperature measurement means comprises a thermocouple in operative contact with said probe outer surface.

8. A method for detecting the presence of foam in a test sample contained in a test sample container, the test sample having a surface, the method comprising the steps of:
   a) heating the test sample in the test sample container, said test sample having a tempering temperature;
   b) measuring the temperature of the test sample in the test sample container; and
   c) detecting the presence of foaming in the test sample with foam detector means, said foam detector means comprising a detector probe held above the sample and having a measuring surface, the presence of foaming in the test sample being detected by
      i) heating said detector measuring surface to a temperature above the test sample tempering temperature, and
      ii) measuring said detector measuring surface temperature, whereby said detector will indicate contact with foam from the test sample when contact with the foam causes said detector measuring surface temperature to cool to a temperature near to the tempering temperature.

9. A method as in claim 8, wherein said detector probe comprises a substantially cylindrical probe comprised of glass, said measuring surface comprises at least a portion of said substantially cylindrical probe surface, said detector probe comprises heater means for heating said measuring surface, and said detector probe comprises temperature measurement means for measuring the temperature of said measuring surface.

10. A method as in claim 9, wherein said heater means comprises an electrical heater held within said probe, and said detector temperature measurement means comprises a thermocouple in operative contact with said measuring surface.

11. A method for detecting the presence of foam in a test sample contained in a test sample container, the test sample having a surface and having a tempering temperature; the method comprising the steps of:
   a) heating the test sample; substantially continuously measuring the temperature of the test sample in the sample container;
   b) placing a foam detector probe above the test sample surface, said detector probe having a measuring surface comprised of low thermal mass material, said probe having heater means for heating said measuring surface, having temperature measurement means for substantially continuously measuring said measuring surface temperature;
   c) heating said probe measuring surface to a temperature substantially above the test sample tempering temperature with said heater means, substantially continuously measuring said probe measuring surface temperature with said probe surface temperature measuring means; and
   d) detecting foam from the sample with said foam detector probe when the foam contacts said probe measuring surface and thereby causes said measuring surface temperature to cool to a temperature near the test sample tempering temperature.

12. A method as in claim 11, wherein said probe is substantially cylindrical and comprised of glass, wherein said measuring surface comprises at least a portion of said substantially cylindrical glass probe, said measuring surface heater means comprises an electrical heater contained within said glass probe, said measuring surface temperature measurement means comprises a thermocouple in operative contact with said measuring surface.

* * * * *